United States Patent [19]

Bannister et al.

[11] 4,193,857

[45] Mar. 18, 1980

[54] OXYGEN SENSORS

[75] Inventors: Michael J. Bannister, Glen Waverley; Neil A. McKinnon, North Balwyn; Robert R. Hughan, Glen Iris, all of Australia

[73] Assignee: Commonwealth Scientific and Industrial Research Organization, Campbell, Australia

[21] Appl. No.: 858,328

[22] Filed: Dec. 7, 1977

[30] Foreign Application Priority Data

Dec. 7, 1976 [AU] Australia ............................. PC8395
Aug. 18, 1977 [AU] Australia ............................. PD1302

[51] Int. Cl.$^2$ ......................................... G01N 27/46
[52] U.S. Cl. ............................... 204/195 S; 204/1 T; 264/104; 264/109; 264/61; 264/63; 264/86; 264/319; 264/332
[58] Field of Search ............................ 204/1 S, 195 S

[56] References Cited

U.S. PATENT DOCUMENTS

| 3,843,400 | 10/1974 | Radford et al. | 204/195 S |
| 3,980,543 | 9/1976 | Eckfeldt | 204/195 S |
| 4,046,661 | 9/1977 | Stringer et al. | 204/195 S |
| 4,067,792 | 1/1978 | Semkina et al. | 204/195 S |

FOREIGN PATENT DOCUMENTS

| 2206216 | 8/1973 | Fed. Rep. of Germany | 204/195 S |
| 48083 | 5/1966 | German Democratic Rep. | 204/195 S |
| 7002292 | 8/1970 | Netherlands | 204/195 S |
| 180211 | 7/1966 | U.S.S.R. | 204/195 S |

OTHER PUBLICATIONS

Kiukkola et al., "J. of the Electrochemical Soc.", Jun. 1957, vol. 104, No. 6, pp. 379–387.

*Primary Examiner*—T. Tung
*Attorney, Agent, or Firm*—Sughrue, Rothwell, Mion, Zinn and Macpeak

[57] ABSTRACT

A composite solid electrolyte material for use in oxygen sensors, which comprises a mixture of at least two ceramic constituents, one of which is a good oxygen ion conductor and the other a non-electrolyte, is useful for oxygen sensor fabrication. Particularly, it enables gas analysis oxygen sensors to be produced by conventional techniques because the coefficient of thermal expansion of the composite electrolyte material can be closely matched to the material of a supporting sensor body. The closeness of thermal expansion coefficients means that oxygen sensors can now be formed in the "green" state, then fired.

20 Claims, 7 Drawing Figures

OXYGEN SENSORS

This invention concerns solid electrolyte materials. It also concerns probes incorporating such materials which are used to measure the oxygen potential in high temperature fluids such as gases, molten metals and glass melts.

Measurement of the oxygen potential of fluids using a solid electrolyte is a well-documented technique. It is outlined, for example, in the specification of Australian Pat. No. 466,251 (and in the specifications of the corresponding U.S. Pat. No. 4,046,661, United Kingdom Pat. No. 1,347,973, Canadian Pat. No. 952,983, West German Offenlegungsschrift document No. 2,218,227 and Japanese patent application No. 36,998/72). Those specifications also describe an oxygen probe for use in the measurement of the oxygen potential in molten copper and in other molten metals (and also in hot gases).

Briefly, the oxygen potential measurement technique relies upon the fact that when a body of a solid material having good oxygen ion conductivity, termed a solid electrolyte, is held with opposing faces of the body in contact with materials possessing different oxygen partial pressures, an e.m.f. is established across the body. If one of the oxygen-containing materials is a fluid under investigation and the other is a material of known oxygen concentration, then the e.m.f., E, is given by the relationship $$E = \frac{RT}{nF} \cdot \ln \frac{(pO_2 \text{ (reference material)})}{(pO_2 \text{ (test fluid)})}$$

where
R = the gas constant,
T = the absolute temperature,
n = 4 (the number of electrons transferred per oxygen molecule),
F = the value of the Faraday constant, and
$pO_2$ = the oxygen partial pressure.

This e.m.f. can be measured using current collectors or electrodes placed in electrical contact with the opposing faces of the solid electrolyte body.

When measuring the oxygen potential of hot fluids, the solid electrolyte must also be resistant to temperatures at least as high as those of the fluids being investigated and also, of course, to chemical reactions with those fluids. This has meant that, for molten metal and furnace gas testing, the electrolytes have been ceramic materials such as thoria ($ThO_2$) doped with either calcia (CaO) or yttria ($Y_2O_3$), and zirconia ($ZrO_2$) or hafnia ($HfO_2$) which have been stabilised or partially stabilised with, typically, calcia, yttria, magnesia (MgO) or scandia ($Sc_2O_3$).

To perform the actual measurement of oxygen potential, a variety of devices have been developed. When testing hot gases, a sample of the hot gas may be withdrawn from the major flow path, cleaned (if necessary) of any particulate material which might affect the accuracy of measurement either by mechanical obstruction or by chemical reaction with the solid electrolyte or the exposed electrode, and then presented to one face of the solid electrolyte. Alternatively, and this is the form of device used with liquid metals, the solid electrolyte may be incorporated into a probe which is inserted directly into the hot fluid, i.e., an "in situ" probe. The general construction of sensors used in most in situ probes falls into one of three categories, namely;

(1) a tube having a closed end, formed entirely from the solid electrolyte material (sometimes lengthened, for access to the test region, and/or for cost reasons, by joining to an open ended tube of another material);

(2) a solid electrolyte coating around the end of a refractory tube plugged with a pellet of a reference material, e.g. nickel/nickel oxide;

(3) a pellet or disc of the solid electrolyte material (a) held mechanically in a fused quartz tube or other type of non-conducting ceramic tube, (b) brazed or cemented into a metal tube; or (c) bonded by a cement or sealed by fusion in or to a non-conducting ceramic tube.

It should be noted that, although sensors having a tubular structure have been referred to in these categories, the tubular body of the sensor need not be of uniform or circular cross-section, nor need the wall or walls of the tube be of uniform thickness. Indeed, the shapes of sensors are increasing in their variety as oxygen probes are constructed for specific applications. For example, generally conical or thimble-shaped sensors and also discs have been used in automobile exhaust gas analysers. In practice, the body of the sensor must ultimately be of a generally hollow, but internally accessible, configuration. The term "hollow body" will be used in this specification on the understanding that it has this more specific connotation.

In part, it was to overcome problems associated with an oxygen probe of the fusion-sealed type of the third category above that the material of the present invention was developed, and an improved form of in situ oxygen probe of this type was realised.

The aforementioned specification of Australian Pat. No. 466,251 describes an oxygen probe formed by the fusion sealing of a pellet of a zirconia-based solid electrolyte into the end of an alumina, mullite or aluminous porcelain tube, the electrodes being mounted to measure the electrical potential developed across the electrolyte pellet. That probe, as already noted (and particularly that form of probe fabricated with an aluminous porcelain tube), has been found especially useful in the measurement of the oxygen potential of molten copper, due to its satisfaction performance and low cost.

The probes made in accordance with the fusion sealing technique of Australian Pat. No. 466,251 have electrolyte pellets which are extensively microcracked. These cracks are of no concern for measurements in molten copper, since they are too fine to be easily penetrated by the copper. However, gases can readily leak through the cracks, causing errors when the probes are used for gas analysis, particularly the analysis of gases with low oxygen content. Of the three tubing materials alumina, aluminous porcelain and mullite, the least microcracking, and thus the most leak-tight assembly, is obtained with alumina. However, with alumina tubes a fair degree of skill is needed to make the seal described in aforementioned Australian specification No. 466,251, and even with skilled operators about 50 percent of the seals so made are incomplete or otherwise faulty. Furthermore, the microcracking in the electrolyte makes the pellet susceptible to spalling under thermal cycling or thermal shock conditions, and thus the probes have restricted lives under severe in situ gas measurement conditions.

Detailed investigation of this problem of pellet cracking during the fusion sealing operation has shown that the cracking is, to a considerable degree, a consequence of the heating and cooling cycle involved in the sealing operation. Tensile stresses generated on cooling from the sealing temperature, due to the different linear expansion coefficients of the zirconia electrolyte and the alumina tubing, cause cracking of the electrolyte, The coefficients are $13\times10^{-6}$ deg $C^{-1}$ (average value from ambient up to sealing temperature) for the electrolyte and (over the same temperature range) about $10\times10^{-6}$ deg $C^{-1}$ for alumina. Aluminous porcelain and mullite have even lower coefficients of linear expansion. When the tensile stresses in the electrolyte exceed the fracture stress, cracks are formed in the electrolyte. Cracks do not occur in the alumina tube, for ceramics are generally stronger in compression than under tension.

Various mechanisms for reducing stresses in the electrolyte were tried. One approach was to reduce the wall thickness of the tubing to lower the stresses in the electrolyte and increase those in the tubing. Others were to replace the zirconia-based electrolyte with (a) a hafnia-based electrolyte having a slightly lower expansion coefficient and (b) a partially stabilised zirconia (PSZ) electrolyte having a composition chosen so that it has an average coefficient of linear expansion close to that of the tubing. (PSZ electrolytes, it may be noted, are limited in their maximum use temperature by consequent changes in microstructure and ensuing degradation). All the methods of reducing stresses met with varying quantitative degrees of success but could not be described as totally satisfactory.

BRIEF DESCRIPTION OF THE DRAWINGS

FIGS. 2-7 are sectional views which illustrate alternative constructions of sensors formed in the "green" state, specifically:

FIG. 3(a) is a cross-sectional view of a mold to prepare a composite electrolyte as shown in FIG. 3(b), FIG. 3(b) showing in cross section the resulting composite electrolyte in closed tube form, the phantom lines in FIG. 3(b) representing material abraded and cut away.

One objective of the present invention is the provision of a solid electrolyte material which successfully avoids the cracking problem associated with the production of oxygen sensors having a pellet of electrolyte material fusion sealed into the end of a non-electrolyte ceramic tube. A second objective, having developed this solid electrolyte material, is the production of an oxygen sensor which is cheaper to make, stronger and more resistant to thermal shock than existing fusion-sealed oxygen sensors. A third objective, also made possible by the solid electrolyte material of the present invention, is the production of an oxygen sensor having a solid electrolyte tip at or near the end of a non-electrolyte ceramic tube or other hollow body, by conventional ceramic fabrication techniques not involving fusion sealing.

Essentially, the present objectives are realised by forming a solid material which contains an intimate mixture of fine particles of at least one oxygen ion conductor (such as doped thoria or stabilised or partially stabilised zirconia or hafnia) and the non-electrolyte ceramic material which forms the hollow body of the oxygen sensor. If the proportions of the electrolyte and non-electrolyte phases or constituents are chosen appropriately, a strong material is obtained having both satisfactory electrolyte properties and a thermal expansion coefficient close to that of the non-electrolyte ceramic material used for the body of the oxygen sensor.

It is also within the scope of this invention to dilute the non-electrolyte ceramic material in the body of the oxygen sensor with constituents of the oxygen ion conducting phase (for example with pure or doped thoria, or with stabilised or unstabilised zirconia or hafnia), the amounts of these additions generally being insufficient to turn the body of the sensor into a good oxygen ion conductor, in order to strengthen or toughen the body of the sensor and/or to effect an even closer thermal expansion match between the non-electrolyte body and the solid electrolyte tip of the sensor.

The material of this invention (hereinafter referred to as a composite electrolyte), comprising a mixture of electrolyte and non-electrolyte phases or constituents, has enabled the construction, by the fusion-sealing technique, of leak-tight "pellet-in-tube" sensors which are suitable for use in measuring the oxygen potential or oxygen content of molten metals and hot gases. Furthermore, it has enabled oxygen sensors having a solid electrolyte tip and a non-electrolyte body to be fabricated by a technique previously unavailable for this purpose, namely, the construction of a sensor in the "green" condition by conventional ceramic forming methods, followed by firing to yield the sensor for actual use. If this "green" forming and firing approach is adopted with the materials hitherto used for solid electrolytes and ceramic tubes, the difference in coefficient of thermal expansion between the electrolyte tip and the tube body causes severe cracking in the electrolyte tip and at the electrolyte/tube boundary as the fired sensor is cooled to ambient temperature. In such a case, the tip generally breaks away, but if it does remain intact the sensor thus formed is so fragile and prone to leaks that it is useless.

A further advantage obtained in using the composite electrolyte of the present invention is that, in part by the dilution with a non-electrolyte material and in part by the ability to fabricate a sensor having only an active tip containing the solid electrolyte, sensors may be constructed using limited or minimal quantities of solid electrolyte materials. Since the electrolyte is considerably more expensive than the supporting ceramic tube or hollow body, this means that electrolytes previously rejected on cost grounds for use in probe assemblies—for example, with a rare earth oxide or with a mixture of rare earth oxides (with or without one or more of the commoner dopants or stabilising compounds being present)—can now be used for oxygen sensors without the probe being prohibitively expensive. The use of such less common dopants and/or electrolytes is of particular value in the construction of low temperature gas analysis probes, such as those required for use in the monitoring of automobile exhaust gases.

Of course, the composite electrolyte of the present invention may also be used to fabricate complete tubes, either open or closed-end, for use as oxygen sensors and the coatings or disc used in prior art sensors.

Thus, according to the present invention, a composite solid electrolyte material comprises a mixture of at least one non-electrolyte constituent or phase and at least one constituent or phase which is a good oxygen ion conductor, the microstructure of the composite material consisting of an intimate mixture of fine grains of the oxygen ion conducting and non-electrolyte constituents, the oxygen ion conducting constituent grains of which comprise from 25 to 75 percent by volume of the mixture.

Also according to the present invention, an oxygen probe comprises a pair of electrodes separated by a composite solid electrolyte material, characterised in that the composite electrolyte material is a mixture of at least one non-electrolyte constituent or phase and at least one constituent or phase which is a good ionic conductor, the microstructure of the composite material consisting of an intimate mixture of fine grains of the oxygen ion conducting and non-electrolyte constituents, the oxygen ion conducting constituent grains of which comprise from 25 to 75 percent by volume of the mixture.

Further, according to the present invention, a ceramic sensor for use in an oxygen probe comprises a closed end non-electrolyte hollow body having formed therein a small region of a composite solid electrolyte material, characterised in that the composite electrolyte material of the small region is a mixture of at least one constituent or phase which is a good ionic conductor and at least one constituent or phase which is the same material as the non-electrolyte which forms the hollow body, and further characterised in that the microstructure of the composite electrolyte material of the small region consists of an intimate mixture of fine grains of the oxygen ion conducting and non-electrolyte constituents, the content of oxygen ion conducting phase grains being from 25 to 75 percent by volume of the mixture.

Preferably, the content of the oxygen ion conducting constituent(s) in the composite solid electrolyte material is from about 30 to about 60 percent by volume. More preferably, it is from 30 to 50 percent by volume.

The non-electrolyte material used for the body of the sensor and as the non-conducting diluent in the composite solid electrolyte is preferably alumina, aluminous porcelain or mullite.

Incidentally, it is recognised that materials described in this specification as "non-electrolytes" or "non-conducting" ceramic materials (such as alumina, mullite and aluminous porcelain) are, in fact, ionic conductors under conditions of high temperature. However, their conductivity is very small compared with that of the materials described as solid electrolytes in this specification, and thus use of the term "non-electrolyte" will not be confusing to persons skilled in this art.

The oxygen ion conducting material used in the composite solid electrolyte may be thoria doped with calcia, yttria or various rare earth oxides, or zirconia or hafnia stabilised or partially stabilised with calcia, magnesia, yttria or other rare earth oxides, either singly or in combination, provided that no adverse reactions occur between the electrolyte and non-electrolyte phases or constituents, leading to a loss of ionic conductivity or unusual thermal expansion behaviour.

In a preferred embodiment of this invention, suitable for use in severe oxygen sensing situations (examples are given below), the non-electrolyte used for the body of the sensor, and as the non-conducting diluent in the composite solid electrolyte, is alumina, and the oxygen ion conducting material is zirconia stabilised or partially stabilised with yttria, the yttria content of the zirconia-yttria material being in the range of from about 4 to about 25 mole percent $Y_2O_3$ (7 to 38 percent by weight). A more restricted range of yttria content, namely from about 6 to about 15 mole percent $Y_2O_3$ (10.5 to 24.5 percent by weight), is preferred since in this range of yttria content there is no reaction between the yttria and the alumina diluent, yet the zirconia is fully stabilised; however, minor amounts of unstabilised zirconia (found with an yttria content below about 6 mole percent) or the compound $3Y_2O_3.5Al_2O_3$ (formed during firing if the yttria content is above about 15 mole percent) may be tolerated, provided the fired body contains from about 25 to about 75 percent by volume of the stabilised zirconia phase.

An oxygen probe made in accordance with the present invention with a pellet, disc or small tip region of composite electrolyte fusion sealed or otherwise bonded to or formed in the end of a hollow body of alumina, aluminous porcelain or mullite, will normally have the probe electrodes mounted to enable the electrical potential across the pellet, disc or tip to be measured. The alternative sensor construction, in which the complete hollow body is fabricated from composite electrolyte material, will again have, usually, the conventional construction of one electrode mounted in contact with the inner surface of the sensor, and the other electrode in contact with the outer surface of the sensor. A protective sheath may be provided around each form of sensor, with apertures to allow the fluid under investigation to contact the outer surface of the composite electrolyte. Such a protective sheath may, in some cases, be the outer or forward electrode of the probe.

For a better understanding of the present invention, examples of solid electrolyte materials and their use in oxygen probes will now be given, after a discussion of the construction of oxygen probes. Reference will be made to the accompanying drawings, of which FIG. 1 is a sectional view of the sensing head of a "pellet-in-tube" oxygen probe, and FIGS. 2 to 7 are sectional views which illustrate alternative constructions of sensors formed in the "green" state.

Figure 1:
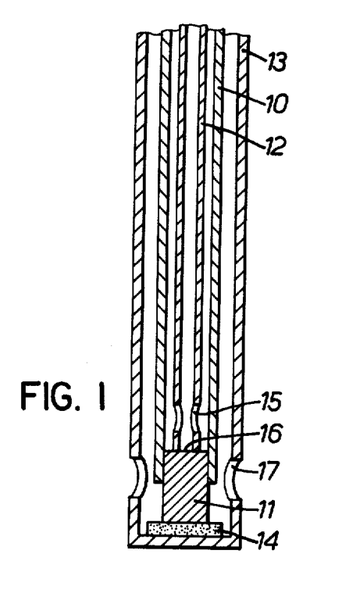
FIG. 1 is a sectional view of the sensing head of a "pellet-in-tube" oxygen probe.
Figure 2A:
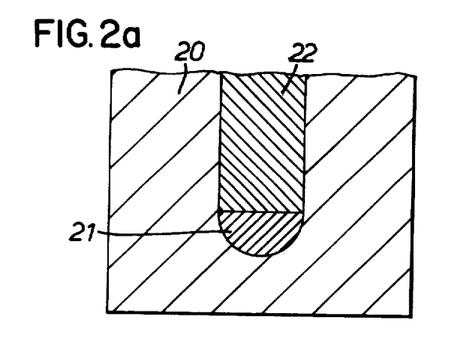
FIG. 2(a) shows a closed-end tube being prepared in a gypsum mold.
Figure 2B:
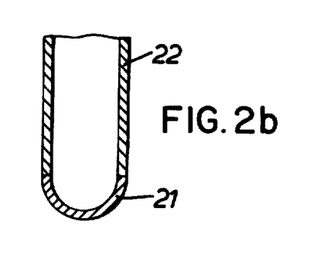
FIG. 2(b) shows the closed-end tube formed per the procedure in FIG. 2(a).

In FIG. 1, a non-conducting ceramic tube 10 has a pellet or disc 11 of composite electrolyte material fusion sealed or otherwise bonded into the end of it. Various alternative electrode arrangements are then possible, including the illustrated tubular inner electrode 12 and the outer electrode assembly consisting of electrode pad 14 supported in position in contact with the pellet 11 of composite electrolyte material by the electrically conducting protective sheath 13. Among these alternatives are binding a wire electrode material around grooves cut into the free (outer) end of the composite electrolyte pellet, and constructing the protective sheath of a suitable electrode material, thus avoiding the need for electrode pad 14.

A further alternative is to coat both the outer and inner faces of the composite electrolyte pellet with a porous layer of a suitable electrode material, for example platinum, and to make electrical connections to these layers (or to extensions of the layers along the non-conducting tube 10 away from the composite electrolyte pellet) using conducting wires, tubes or rods. A further alternative again is to use wires sintered, embedded or otherwise fixed into holes at either end or both ends of the composite electrolyte pellet.

The inner electrode (a conducting tube 12 in the illustrated embodiment) is pressed or biassed (generally with a spring) against the inside surface of composite electrolyte pellet or disc 11. If the illustrated tubular inner electrode is used, it will generally be provided with an aperture 15 near its tip 16, and a reference gas is passed down the tube 12, through aperture 15, to leave the probe after passage up (or along, depending on the orientation of the probe when in use) the ceramic tube 10. Reference gas flow in the opposite direction (for example, through the annular gap between tubes 10 and 12 and out through tube 12) is also possible. A further alternative is to maintain the reference gas on the outside of sensor tube 10, and to convey the gas under examination to the inner electrode.

If a protective sheath 13 is used with the probe and it is to be used for gas analysis with the gas to be analysed on the outside of the probe, a plurality of apertures 17 are provided in the sheath to enable the gas being analysed to flow past the pellet 11 of electrolyte material.

As noted above, other constructions of probe are possible, including (a) the use of a sensor formed entirely in the "green" state, then fired (these are discussed in more detail later), (b) the use of a single, closed-end-tube of composite electrolyte material, and (c) the use of a sensor of category (2) type referred to in the introductory part of this specification.

The materials that may be used for electrodes will depend on the use to which the probe is to be put. Platinum has often been used in the past, but in atmospheres which attack platinum, other noble metals such as gold, or alloys of chromium with nickel and/or iron, such as Inconel, Incoloy, Nichrome or stainless steel, may be used. If an alloy of chromium with nickel and/or iron is used as either electrode, pre-oxidation at high temperatures is needed if spurious, e.m.f.s are not to be observed when the probe is first used. However, such pre-conditioning of the electrode is not essential; the alloy electrode will rapidly adopt an inert oxide coating in use, and on formation of that coating the spurious e.m.f.s will not be observed. A chromium-alumina cermet may also be used as either electrode in configurations such as the pad 14 or protective sheath 13, shown in this case at the external electrode.

The following examples illustrate the preparation and properties of the new composite electrolyte material of this invention and oxygen sensors made with the material by both the conventional or known techniques and by the "green" forming route.

EXAMPLE 1

A bath of zirconia containing 6 mole percent $Y_2O_3$ as stabiliser was prepared by a coprecipitation process. Coprecipitation gives a very fine, intimate mixture of the zirconia and yttria, which react to form a stabilised zirconia solid solution at quite low temperatures. By crushing, sieving and calcining at about 800° C., fine particles of the solid solution are obtained. The coprecipitated powder was ground in an alumina mortar to less than 200 mesh (B.S.S.), calcined in air at 800° C. for 1 hour, and blended with "Linde A" alumina powder in quantities calculated to give volume fractions of electrolyte of 0.50, 0.40, 0.30 and 0.20 in the sintered body. In calculating these mixtures it was assumed that the theoretical density of the zirconia-6 mole percent $Y_2O_3$ solid solution was 5.97 $g/cm^3$ and that the mixtures could be sintered to zero porosity. Total masses of 10 g of powder were prepared at each composition, and each mixture was blended dry for two hours in a mechanical shaker using plastic containers and two acrylic balls. 5 percent by weight of water was then added, and blending continued for a further 10 minutes. Each mixture was then isostatically pressed at 30,000 psi to give a cylindrical bar about 6 cm long and 8 mm diameter. These bars were sintered in air at 1700° C. for 15 hours, using an alumina boat.

To determine the characteristics of these materials, the following tests were performed:

1. The electrical resistance of each specimen was determined in air, in a laboratory muffle furnace, over the range 500° to 900° C. using a simple two-terminal technique.

2. The rods were machined to a diameter of about 5 mm and the densities determined by mercury displacement and by mensuration.

3. Each rod was broken in a four-point bending rig and the modulus of rupture calculated.

4. A small slice from the end of each rod was mounted and polished for optical microscopy and X-ray diffraction.

5. The thermal expansion behavior of a 1-inch length of each rod was determined in a dilatometer calibrated against vitreous silica to 1000° C., and previously used to determine the expansion behavior of alumina tubing.

The densities, bend strengths, and electrical conductivity results are tabulated below.

| Volume Fraction Stabilised Zirconia | 0.50 | 0.40 | 0.30 | 0.20 |
|---|---|---|---|---|
| Mass Fraction Stabilised Zirconia | 0.60 | 0.50 | 0.39 | 0.27 |
| Density (mercury displacement) $g/cm^3$ | 4.74 | 4.58 | 4.42 | 4.24 |
| Density (Mensuration), $g/cm^3$ | 4.72 | 4.54 | 4.41 | 4.25 |
| Theoretical density, $g/cm^3$ | 4.98 | 4.78 | 4.58 | 4.38 |
| Modulus of rupture, psi. | 26,400 | 27,300 | 32,100 | 34,500 |
| Activation energy for electrical conductivity, kcal/mol. | $23.0 \pm 0.3$ | $25.7 \pm 1.1$ | $23.3 \pm 0.2$ | $23.8 \pm 0.7$ |
| Conductivity at 900° C., $\Omega^{-1} cm^{-1}$ | $5.1 \times 10^{-3}$ | $1.7 \times 10^{-3}$ | $5.8 \times 10^{-4}$ | $1.6 \times 10^{-5}$ |

The densities of these specimens all lay in the range 95 ∝ 97 percent of theoretical. The modulus of rupture was comparable with values previously determined using an undiluted $ZrO_2$-6 mole percent $Y_2O_3$ electrolyte.

The activation energy for electrical conductivity was independent of composition and compared well with accepted values for the undiluted electrolyte, suggesting that conduction occurred via the yttria-stabilised zirconia constituent. This conclusion was supported by the reduction in conductivity with decreased zirconia content.

Optical microscopy showed all the specimens to be similar in containing a fine intergrowth of alumina and yttria-stabilised zirconia, together with isolated areas of yttria-stabilised zirconia. X-ray diffraction patterns taken before and after sintering could be completely indexed in terms of $\alpha$-$Al_2O_3$ and cubic zirconia with lattice parameter 5.13 Å. There was no additional phase formed in the sintered material.

Thermal expansion results over the temperature range 20° to 1000° C. showed that the best match with alumina occurred for 0.50 volume fraction of electrolyte; however the match was still good for the other compositions and up to fusion sealing temperatures (about 1900° C.) the better overall agreement probably occurred with the lower electrolyte compositions. Fracture strains of ceramics are typically 0.1 percent, so that the differences in fractional thermal expansion should be within $1 \times 10^{-3}$ to adequately limit cracking. All the expansion curves agreed with the curve for alumina tubing within $5 \times 10^{-4}$, up to 1000° C.

All of the compositions were readily sealed into alumina tubing. A slight modification to the technique recited in aforementioned specification No. 466,251 was required in that, to avoid melting the composite electrolyte pellet, the oxy-acetylene flame had to be directed mainly on the alumina tubing. Also, compared with previous experience using the conventional electrolyte pellets (without alumina present), there was less tendency for the pellet to draw into the tube as the seal was made. Because of the good thermal expansion match between pellet and tubing it was also found that there was no longer any need to provide a closely controlled minimum clearance prior to sealing.

EXAMPLE 2

Twelve oxygen sensors of the type illustrated in FIG. 1 of the accompanying drawings were made by sealing short lengths of the composite electrolyte rods described in Example 1 (three sensors of each electrolyte composition) into alumina tubing. These sensors were tested by internal pressurisation with air at 30 psig, the vacuum leak rate was determined at temperatures up to 1200° C., and the cell voltage against both oxygen and air references was determined in a 50 percent CO, 50 percent $CO_2$ atmosphere at 1100°, 1200° and 1300° C., and in nitrogen at 1100° C.

All twelve sensors gave leak rates under 30 psig air which were less than those of "normal" fusion sealed sensors of the type described and claimed in aforementioned Australian specification No. 466,251, and its equivalents, while occasional sensors showed no leaks at all.

All sensors showed vacuum leak rates which were better than the average behaviour of such "Normal" sensors and comparable with the best. With such 'normal' sensors, the leak rate drops rapidly with increasing temperature; with the present sensors the leak rate was initially much lower and varied only slightly with temperature.

Sensors were sectioned to expose the junction of the composite electrolyte and the alumina tube and examined by optical microscopy. There was no cracking at all in the composite solid electrolyte pellets and only minor cracking in the alumina tubing.

When the sensors were tested in $CO/CO_2$ atmospheres and nitrogen, they all gave cell voltages comparable with those obtained from 'normal' sensors. In fact, the experimental sensors gave higher voltages than customary in nitrogen, a sign that the lower leak rate makes them better suited to measurements of inert gases. The electrical resistivity was greater than that of sensors made using undiluted electrolyte pellets, but only at 0.20 volume fraction of electrolyte in the composite material was it considered to be unacceptably high.

EXAMPLE 3

A batch of fifty-six "pellet-in-tube" sensors was made using pellets containing alumina with 0.40 volume fraction $ZrO_2$-6 mole percent $Y_2O_3$. The sealing success rate was 82 percent, as judged by their leak rates and good performance in test gases of nitrogen and 50 percent CO, 50 percent $CO_2$. (Incidentally, the 18 percent 'failed' tubes need not be wasted—the host tube is available for re-use after cutting off the composite electrolyte pellet). Samples of the successfully sealed sensors were tested by continuous use for periods of up to 6 months in the following industrial applications:

(a) a reducing atmosphere metal sintering furnace, in which the furnace gases contained zinc vapour from a zinc stearate pressing aid in the metal powders, (b) a large, coal-fired rotary kiln in which ilmenite concentrates are reduced to rutile and metallic iron, (c) a steel soaking pit, (d) a reverberatory furnace smelting copper concentrates, in which a probe was used as an aid to the control of solid fuel additions, and (e) various other gas-fired furnaces and kilns, with a probe used for on-line monitoring and control of combustion stoichiometry.

Of these applications, (a), (b) and (d) would be regarded as severe oxygen sensing situations.

In each case the sensor performed accurately and reliably in conditions needing a rugged, high-integrity, oxygen potential measuring device, despite, in some instances, temperatures as high as 1600° C., contaminants such as sulphur and zinc vapour in the gases, and direct contact with materials such as partly-reduced ilmenite. In evaluations such as (e), it was found that the probes could be thrust repeatedly into gas flames at temperatures of up to at least 1600° C. without spalling or failure of the sensor. Similar treatment given to sensors made using pellets of the undiluted electrolyte caused spalling of the electrolyte pellet. The better performance of the sensors made using the composite electrolyte material of the present invention is indicative of an increased resistance to thermal shock, and is consistent with the absence of cracking in the pellets after sealing.

EXAMPLE 4

Composite solid electrolyte pellets for use in oxygen sensors were made from mixtures of "Linde A" alumina powder and the following alternatives to the yttria-stabilised zirconia coprecipitate used in Examples 1, 2 and 3.

(a) "Zyttrite", an alkoxy-derived stabilised zirconia powder containing 6.9 mole percent $Y_2O_3$, obtained from Wright-Patterson Air Force Base (powder "A");

(b) an yttria-stabilised zirconia powder containing 6 mole percent $Y_2O_3$ supplied by Magnesium Elektron Limited (powder "B"); and (c) a mixture of unstabilised zirconia powder purchased from Ugine Kuhlmann and yttria powder purchased from the American Potash and Chemical Corporation, with the proportions of zirconia and yttria chosen to yield a stabilised zirconia containing 7 mole percent $Y_2O_3$ (powder "C").

All the powders were heated in air to form or partly form the cubic zirconia solid solution prior to mixing with alumina. For powder "A", one hour at 800° C. was sufficient, whereas for powders "B" and "C", two hours at 1000° C. and one hour at 1100° C., respectively, were required.

Rods of alumina containing 0.30, 0.40 and 0.50 volume fraction of yttria-stabilised zirconia were prepared from powders "A", "B" and "C" using the technique outlined in Example 1. The fired rods were characterised by X-ray diffraction, optical microscopy and the measurement of density, electrical resistance, modulus of rupture and thermal expansion as described in Example 1.

All three alternative sources of stabilised zirconia gave composite electrolyte having similar properties to those of Example 1. There were minor differences in grain size depending on the powder used, and in the magnitude of the electrical conductivity, but all the compositions were considered suitable for sealing into alumina tubing to form oxygen sensors. Subsequent trails using two or three pellets cut from each rod showed that all compositions could be successfully fusion sealed into alumina tubing.

EXAMPLE 5

Mixtures of zirconia, yttria and alumina were prepared (a) by coprecipitation of the hydroxides and (b) by mixing the three oxide powders to give 50 weight percent alumina and from 5.7 to 40 mole percent $Y_2O_3$ (10 to 55 weight percent) in the zirconia. The various mixtures were pressed into pellets and fired at 1700° C. in air for two weeks, with an intermediate cooling to ambient temperature, grinding and repelleting after the first week. X-ray diffraction was used to identify the compounds present in the mixtures after firing.

It was established that a two-phase equilibrium at 1700° C. exists between alumina and stabilised zirconia for yttria levels in the zirconia from about 6 to about 15 mole percent $Y_2O_3$ (10.5 to 24.5 percent by weight). Unstabilised zirconia was present with yttria levels below this range. With yttria levels above 15 mole percent $Y_2O_3$, the compound $3Y_2O_3.5Al_2O_3$ was produced. Extensive formation of either unstabilised zirconia or $3Y_2O_3.5Al_2O_3$ is detrimental to the oxygen ion conductivity of the solid electrolyte. Thus zirconia with a $Y_2O_3$ concentration outside the range 6 to 15 mole percent becomes progressively less useful in the present invention as the concentration departs from the range boundaries.

EXAMPLE 6

A mixture of 50 parts by weight of "Linde A" alumina and 50 parts by weight of yttria-stabilised zirconia coprecipitate containing 6 mole percent $Y_2O_3$ was dispersed in 50 parts by weight of water and five parts by weight of Dispex A40 (an organic deflocculant) and slip-cast to form closed-end tubes using gypsum moulds in a conventional manner. Firing at 1800° C. for 2 hours in a natural gas-air-oxygen furnace gave high density, impervious tubes with sufficient oxygen ion conductivity to be used as oxygen sensors. The presence of alumina gave these sensors an improved resistance to mechanical and thermal shock when compared with sensors construction fabricated from undiluted electrolyte materials.

EXAMPLE 7

An alumina slip (Slip A) was produced by dispersing "Linde A" alumina in water in the proportions 100 parts by weight of alumina to 50 parts by weight of water. 1.7 parts by weight of "Displex A 40" were used as a deflocculant and the slip was ball milled for twelve hours. A stabilized zirconia slip (Slip B) was also prepared using 100 parts by weight of a zirconia—6 mole percent $Y_2O_3$ co-precipitate, previously calcined in air at 700° C. for 30 minutes, 50 parts by weight of water, and 8 parts by weight of "Dispex A 40". In this case the constituents were hand mixed using a mortar and pestle. Equal masses of the alumina slip and the stabilized zirconia slip were then blended together to form Slip C, containing approximately equal proportions by weight of alumina and yttria-stabilized zirconia.

A closed-end tube, consisting of a composite electrolyte composition at the closed end and an alumina composition for the main body, was then prepared by slip-casting in a gypsum mould, as illustrated in FIG. 2, in the following manner.

A small quantity of Slip C (reference 21 in FIG. 2a) was first deposited at the closed end of the mould 20 using a long syringe. The remainder of the mould cavity was then gently filled with Slip A (reference 22). After allowing the time necessary to build up the desired thickness of the casting, the mould was carefully inverted and the excess slip was allowed to drain out. The closed-out tube thus formed, illustrated in FIG. 2b, was then fired.

Since it is necessary for the cast-up composite electrolyte to be exposed internally in the tube after draining, it is important that an appropriate predetermined and measured quantity of Slip C is admitted to the mould in the first instance. An insufficiency of Slip C will lead to complete covering of the cast-up composite electrolyte by an overlay of alumina from the main body slip. Excess composite electrolyte slip will cause undesirable contamination of the drained slip, which is normally returned to the batch of Slip A (which is generally made up to fabricate a number of closed-end tubes).

Some control over the casting rate of each slip is necessary to ensure that the relative lengths of the composite electrolyte tip and the main body are within the desired limits. Such control can be exercised by varying the permeability of the casts, which in turn is achieved by varying the grain size of the powders used and/or the degree of deflocculation of the slips.

The area of composite electrolyte exposed within the tube may be varied within limits by allowing for a greater or lesser amount of uncast composite electrolyte slip at the stage when draining begins. Gentle rotation of the mould during draining may be used to effect an even deposition of excess composite electrolyte slip over the inside of the tube, if so desired.

EXAMPLE 8

Figures 3A, 3B:
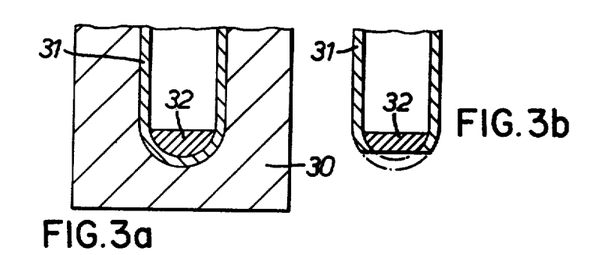

Slips A, B and C were prepared as described in Example 7. A gypsum mould 30 (FIG. 3a) was then filled with Slip A, allowed to stand for the time needed to deposit the required thickness of cast and drained in the normal manner. Immediately after draining had ceased, the mould 30 was righted and a measured quantity of Slip C was admitted to the inside base of the cast tube 31, using a long syringe. The amount of composite electrolyte slip so admitted was predetermined in order to leave an integrally formed button 32 of composite electrolyte within the tube. This button was subsequently exposed externally, as shown in FIG. 3b. In separate experiments, successful exposure was achieved by abrading and by cutting away the layer of alumina at the end of the tube, before and after firing. Successful closed-end tubes were also prepared by righting the mould and admitting Slip C just before completion of the draining.

EXAMPLE 9

Slips A, B and C were prepared as described in Example 7.

In this case the gypsum mould 40 (FIG 4a) was provided with a means of entry to the inside bottom of the cavity, namely, a length of narrow tubing 41 cast into the mould (but not extending beyond the inner surface of the mould).

Figures 4A, 4B:
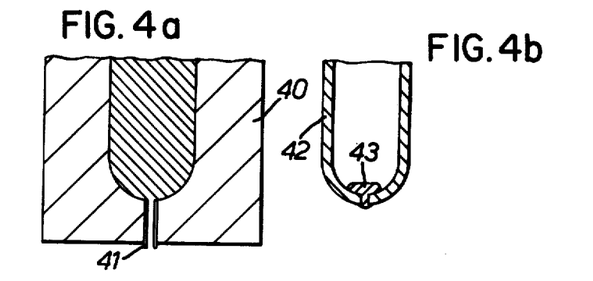
FIG. 4(a) shows a gypsum mold in cross section used to form a closed-end tube of alumina as shown in FIG. 4(b) provided with composite electrolyte layer 43.

A closed-end tube 42 of alumina was cast conventionally in mould 40 using Slip A.

During this operation the bottom entry tube 41 was sealed at its external end, and in the process of casting the inner end of this tube 41 became partly or wholly sealed over with solidified casting slip. Draining of the cavity was then performed by inversion of the mould 40 in the usual way (in fact, draining could have been effected through the bottom entry tube by puncturing the accumulated cast at its inner end). Either just before, or soon after draining was complete, the bottom entry tube 41 was connected to a reservoir of Slip C, in the form of a graduated syringe, and a predetermined quantity of slip C was admitted to the interior of the cast, using sufficient pressure to force its entry. In some instances, an excess of Slip C was used to coat the inside of the body of the alumina tube 42 with a composite electrolyte layer 43, by gently rotating the mould to spread the composite electrolyte. The tubes formed by this technique were fired.

The technique recited in this Example has a possible advantage over the technique of Examples 7 and 8 since it provides a small external exposure of composite solid electrolyte material (as small as the diameter of the bottom access tube) in the finished tube, while retaining a large internal exposed composite electrolyte surface.

EXAMPLE 10

Figure 5A:
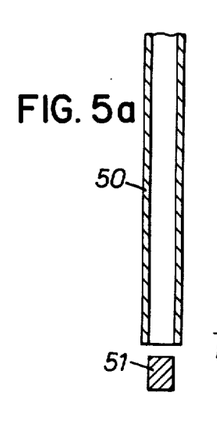
FIG. 5 shows an open-end alumina tube 50 provided with pellet 51 cut from a composite electrolyte rod.

An open-end alumina tube 50 (FIG. 5a) was extruded in a conventional manner using a mixture containing 100 parts by weight of "Linde A" alumina, 30 parts by weight of water, 2 parts by weight of gelatin, 2 parts by weight of glycerol and 2 parts by weight of poly(ethylene glycol). A solid rod of composite electrolyte material, with a diameter slightly less than the inside diameter of the extruded alumina tube, was also extruded using a mixture containing 50 parts by weight of "Linde A" alumina, 50 parts by weight of zirconia—6 mole percent $Y_2O_3$ co-precipitate previously calcined in air at 700° C. for 30 minutes, 30 parts by weight of water, 2 parts by weight of gelatin, 2 parts by weight of glycerol and 2 parts by weight of poly(ethylene glycol).

In other experiments, the glycerol, gelatin and poly(ethylene glycol) were used singly or in pairs to effect the desired degree of plasticity for a given size of extrusion of both the alumina and the composite electrolyte material.

Figure 5B:
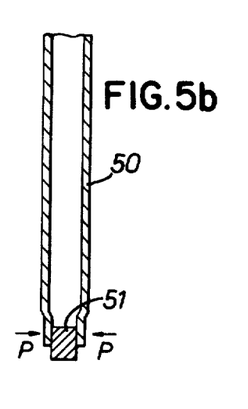
Figure 6:
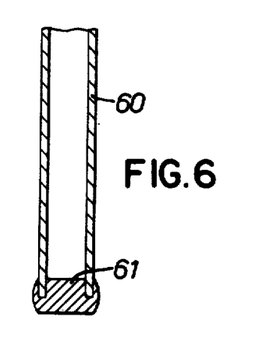
FIG. 6 shows an open-end alumina tube 60 extruded as described in Example 10 with one end being closed with a small pellet 61 of composite electrolyte mixture.

A pellet 51 was cut from the composite electrolyte rod (conveniently a pellet approximately equal in length to the diameter of the rod was used) and was fitted into one end of the extruded alumina tube 50. A circumferential pressure P was used to ensure a firm and even contact between the composite electrolyte pellet and the inner surface of the alumina tube. Depending on the ultimate application of the sensor, the pellet was positioned either flush with the end of the tube or with a portion protruding beyond the end of the tube (as shown in FIG. 5b). The tube was then fired.

EXAMPLE 11

An open-end alumina tube 60 (FIG. 6) was extruded as described in Example 10. One end of the tube was closed with the mixture used in Example 10 for extruding a rod of composite electrolyte material, by pressing a small 61 pellet of the composite electrolyte mixture into the end of the tube and smearing the mixture over the outer wall of the tube, adjacent to the end to be closed, to effect a good bond between the alumina and the composite electrolyte mixture. The tube was then fired.

EXAMPLE 12

Figure 7:
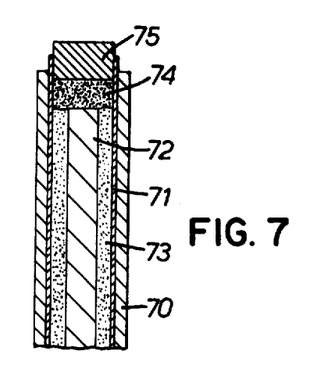
FIG. 7 shows a short alumina tube with a composite solid electrolyte tip formed by isotactic pressing as described in Example 12.

A short alumina tube with a composite solid electrolyte tip was made by isostatic pressing in the following manner (see FIG. 7).

Conventional tooling, comprising a vented plastic tube 70 (a metal tube could have been used) with a rubber bag liner 71, was used to contain the powder 73 to be formed into the alumina tube. A metal mandrel 72, held concentric with the vented tube 70 by means of a temporary bridge across the end of the tooling, was used to form the central hole of the sensor tube. "Linde A" alumina powder, spray-dried to improve its die-fill properties, was loaded into the rubber bag 71 until only the tip of the mandrel remained uncovered. The remaining space 74 above the mandril was then filled with a mixture of 50 parts by weight of "Linde A" alumina and 50 parts by weight of a zirconia—6 mole percent $Y_2O_3$ coprecipitate previously calcined in air at 700° C. for 30 minutes. This yttria-stabilised zirconia plus alumina mixture was also spray-dried before use to improve its die-fill properties.

The temporary bridge supporting the mandrel was then removed and the rubber bag was closed with a stopper 75. The tooling, filled now with ceramic powder, was immersed in a suitable liquid in a pressure vessel and pressed isostatically to about 40,000 psi. After release of the pressure the tooling was taken out of the pressure vessel, the bag was opened and the pressed tube and mandrel were removed together. The mandrel was carefully extracted from the pressed body, leaving a closed end tube of alumina with a composite solid electrolyte tip. This tube was subsequently densified by firing at high temperatures.

To fire the tubes of Examples 7 to 12, in order to convert them to sound, impervious bodies for use as sensors in solid electrolyte oxygen probes or analysers, they were heated to 1750° C. and maintained at this temperature for 5 hours, using a furnace burning natural gas. Firing temperatures should not exceed 1850° C., otherwise partial melting will occur due to a eutectic reaction between the alumina and thee yttria-stabilized zirconia.

From the foregoing, it will be clear to those skilled in this art that by the present invention, a composite solid electrolyte material can be produced, for use in oxygen sensors with the following advantages over prior art materials.

1. Pellets of the sintered composite electrolyte are more readily sealed into alumina, aluminous porcelain or mullite tubing to form oxygen sensors. The sealing success rate in alumina tubing is over 80 percent compared with only 50 percent for prior art probes of similar construction.

2. The "pellet-in-tube" sensors so made have greater mechanical integrity than prior art probes of similar construction, and thus have lower leak rates and greater resistance to thermal and/or mechanical shock, factors which produce long sensor lifetimes and enable "in situ" oxygen probes to be used in applications found to be beyond the capability of prior art probes.

3. The composite solid electrolyte material can be used in a new route sensor construction in which the sensor is fabricated "green" and subsequently fired, whereby a sensor is produced with inherently low cost of manufacture and good mechanical properties.

Particularly in respect to the "green" probe route of construction, it should be noted that the use of a limited volume of composite solid electrolyte material at the end of a body of a ceramic material which is not an electrolyte enables and permits accurate positional sampling of a gas stream under test. This is a useful feature where local variations in oxygen concentrations can exist. In addition, because the reduction in usage of expensive solid electrolyte material provides considerable cost advantages over prior art oxygen sensor tubes, oxygen sensing devices produced in this way can incorporate electrolyte materials in which the solid electrolyte oxide is doped, stabilised or partially stabilised by a rare earth metal oxide or a mixture of oxides which includes one or more rare earth metal oxides.

Yet another feature of sensors formed in the "green" state and then fired is that the sensor can be fabricated in various shapes. For example, some automobile exhaust gas sensors use a generally conical sensor element, constructed entirely of electrolyte material. Sensors of the same shape, but made of a non-electrolyte ceramic material with a tip of composite electrolyte at the point of the cone, can readily be fabricated by the "green" sensor construction techniques exemplified above. Such sensors will perform as efficiently as the current sensors in the exhaust gas monitoring system.

We claim:

1. An oxygen sensor comprising a ceramic hollow body composed of or containing a composite solid electrolyte material and a pair of electrodes, one of the electrodes being located within said hollow body and the other being located outside said hollow body, said electrodes being separated by said composite solid electrolyte material, and said composite solid electrolyte material comprising a mixture of at least one non-electrolyte constituent or phase which is selected from the group consisting of alumina, aluminous porcelain and mullite, and at least one constituent or phase which is a good oxygen ion conductor, the microstructure of the composite material consisting of an intimate mixture of fine grains of the oxygen ion conducting and the non-electrolyte constituents, the oxygen ion constituent grains of which comprise from 25 to 75 percent by volume of the mixture.

2. An oxygen sensor as defined in claim 1, in which the content of oxygen ion conducting constituent grains in the composite solid electrolyte material is from 30 to 60 percent by volume.

3. An oxygen sensor as defined in claim 1, in which the content of oxygen ion conducting constituent grains in the composite solid electrolyte material is from 30 to 50 percent by volume.

4. An oxygen sensor as defined in claim 1, in which the oxygen ion conducting constituent of the composite solid electrolyte material is selected from the group consisting of thoria doped with calcia, thoria doped with yttria, zirconia stabilised or partially stabilised with calcia, zirconia stabilised or partially stabilised with magnesia, and zirconia stabilised or partially stabilised with yttria.

5. An oxygen sensor as defined in claim 1, in which the non-electrolyte constituent of the composite solid electrolyte material is alumina and the oxygen ion conducting constituent is zirconia stabilised or partially stabilised with yttria.

6. An oxygen sensor as defined in claim 5, in which the yttria content of the zirconia-yttria conducting constituent of the composite solid electrolyte material contains from about 4 to about 25 mole percent yttria.

7. An oxygen sensor as defined in claim 5, in which the yttria content of the zirconia-yttria oxygen ion conducting constituent of the composite solid electrolyte material contains from about 6 to about 15 mole percent yttria.

8. An oxygen sensor as defined in claim 5, in which the stabilised or partially stabilised zirconia is obtained by the sequential steps of (a) coprecipitation of zirconia and yttria, (b) crushing and sieving the coprecipitate particles to less than 200 mesh B.S.S., and (c) calcining the resulting powder to form a homogeneous solid solution of yttria in zirconia.

9. An oxygen sensor as defined in claim 5, in which the composite solid electrolyte material is produced by the admixture of stabilised or partially stabilised zirconia in finely ground form with alumina powder, followed by consolidating the admixture and firing to a temperature below 1850° C. which is sufficiently high to produce a high density impervious body.

10. An oxygen sensor as defined in claim 5, in which the composite solid electrolyte material is produced by the admixture of finely ground stabilised or partially stabilised zirconia with alumina powder, an organic deflocculant and water, followed by slip casting the admixture in gypsum moulds and firing the solid material so produced at an elevated temperature below 1850° C.

11. An oxygen sensor as defined in claim 1, in which the composite solid electrolyte material is in pellet or disc form, bonded in or to the end of an open tube fabricated from a material selected from the group consisting of alumina, aluminous porcelain and mullite.

12. An oxygen sensor as defined in claim 11, in which the composite solid electrolyte pellet or disc is fusion sealed to the open tube.

13. An oxygen sensor as defined in claim 1, in which the composite solid electrolyte material is in the form of a closed tube.

14. An oxygen sensor as defined in claim 1, formed in the green state so that the composite solid electrolyte material forms a conducting region in a non-electrolyte, ceramic hollow body, then fired.

15. An oxygen sensor as defined in claim 14, in which the hollow body of the sensor contains a proportion of the conducting constituent of the composite solid electrolyte material which is less than the proportion used in the composite solid electrolyte material forming the conducting region.

16. An oxygen sensor as defined in claim 14, in which the same non-electrolyte ceramic material is used for the hollow body and for the non-electrolyte constituent in the composite solid electrolyte material.

17. An oxygen sensor as defined in claim 1, in which said electrode within said hollow body comprises a conducting tube located within the ceramic hollow body, one end of said conducting tube being in contact with the composite solid electrolyte material, at least one aperture being formed in the conducting tube in the region of said end thereof, whereby a gas may be conveyed through the conducting tube before or after passing through the aperture or apertures formed therein.

18. An oxygen sensor as defined in claim 1, in which said electrode outside said hollow body comprises a conducting sheath around the ceramic hollow body, said sheath being in electrical contact with the composite solid electrolyte material, and said sheath having a plurality of apertures to enable a gas to flow from outside the sheath to within the sheath and past the composite solid electrolyte material.

19. An oxygen sensor as defined in claim 1, in which the electrodes are made from a material selected from the group consisting of platinum, gold, an alloy of chromium with nickel, an alloy of chromium with iron, a chromium-alumina cermet, and stainless steel.

20. An oxygen sensor as defined in claim 1, wherein said electrodes are made from a material selected from the group consisting of platinum, gold, an alloy of chromium with nickel, an alloy of chromium with iron, a chromium-alumina cermet, and stainless steel and said oxygen ion conduting constituent or phase is selected from the group consisting of thoria doped with calcia, thoria doped with yttria, zirconia stablised or partially stabilised with calcia, zirconia stabilised or partially stabilised with magnesia, and zirconia stabilised or partially stabilised with yttria.

* * * * *